US012568941B2

(12) United States Patent
Escalante et al.

(10) Patent No.: US 12,568,941 B2
(45) Date of Patent: Mar. 10, 2026

(54) DEVICE FOR SORTING INSECTS, ALLOWING THE SEPARATION OF CRAWLING INSECTS FROM THE REST OF A MIXTURE

(71) Applicant: Ynsect, Évry-Courcouronnes Cedex (FR)

(72) Inventors: Pedro Escalante, Dolores Alicante (ES); Cyril Michel, Janville sur Juine (FR); Mathieu Château, Evry (FR); Manon Chogne, Dijon (FR); Fabrice Berro, Paris (FR); Arturo Escaroz Cetina, Eindhoven (NL); Thibault Sarton Du Jonchay, Chevrières (FR)

(73) Assignee: Ynsect, Évry-Courcouronnes Cedex (FR)

( * ) Notice: Subject to any disclaimer, the term of this patent is extended or adjusted under 35 U.S.C. 154(b) by 0 days.

(21) Appl. No.: 17/925,953

(22) PCT Filed: May 18, 2021

(86) PCT No.: PCT/EP2021/063199
§ 371 (c)(1),
(2) Date: Nov. 17, 2022

(87) PCT Pub. No.: WO2021/233945
PCT Pub. Date: Nov. 25, 2021

(65) Prior Publication Data
US 2023/0180726 A1      Jun. 15, 2023

(30) Foreign Application Priority Data
May 19, 2020     (FR) ........................................ 2005102

(51) Int. Cl.
*A01K 67/30*          (2025.01)
*A01K 29/00*          (2006.01)

(52) U.S. Cl.
CPC .............. *A01K 67/30* (2025.01); *A01K 29/00* (2013.01)

(58) Field of Classification Search
CPC .................................................... A01K 67/033
See application file for complete search history.

(56) References Cited

U.S. PATENT DOCUMENTS 6,056,127 A * 5/2000 Low .......................... B07C 5/02
209/580
6,646,218 B1 * 11/2003 Campbell ............... B07C 5/367
209/582
(Continued)

FOREIGN PATENT DOCUMENTS

CN          105501833 A      4/2016
EP           3415002 A1     12/2018
(Continued)

*Primary Examiner* — Monica L Perry
*Assistant Examiner* — Aaron M Rodziwicz
(74) *Attorney, Agent, or Firm* — Panitch Schwarze Belisario & Nadel LLP; Erin M. Dunston

(57)          ABSTRACT
An insect sorting device, machine, and use thereof, which improves sorting efficacy by prompting the insects to cling onto the belt, comprising a belt conveyor (2) having an upper surface (5) and a lower surface (6) formed by the belt (3) of the conveyor (2). When the belt (3) is turned over to pass onto the lower surface (6) of the conveyor (2) all or some of the insects of a mixture remain attached to the belt (3) while the rest of the mixture falls by gravity. The upper surface (5) of the conveyor (2) being substantially flat and horizontal over a majority of its length between the first end (7) and the second end (8), it comprises an end portion (14), adjacent the second end (8), having a downward inclination, comprised between 20° and 90° relative to the rest of the upper surface (5) of the conveyor (2).

16 Claims, 5 Drawing Sheets

(56)                 References Cited

U.S. PATENT DOCUMENTS

| | | | | |
|---|---|---|---|---|
| 11,001,452 B2 * | 5/2021 | Shaw | ...................... | G01N 21/94 |
| 2002/0079194 A1 * | 6/2002 | Ydoate | .................. | B65G 47/31 |
| | | | | 198/461.3 |
| 2002/0084174 A1 * | 7/2002 | Minardi | ............... | B65G 69/165 |
| | | | | 198/861.2 |
| 2004/0089522 A1 * | 5/2004 | Shaum | ................... | B65G 21/10 |
| | | | | 198/861.1 |
| 2020/0205355 A1 * | 7/2020 | Lemmen | ................ | A01G 18/62 |

FOREIGN PATENT DOCUMENTS

| | | | |
|---|---|---|---|
| FR | 3034622 | B1 | 5/2017 |
| JP | H1159853 | | 3/1999 |
| KR | 101464734 | B1 | 11/2014 |
| KR | 20200040440 | A | 4/2020 |
| WO | WO-2019084554 | A1 | 5/2019 |

* cited by examiner

DEVICE FOR SORTING INSECTS, ALLOWING THE SEPARATION OF CRAWLING INSECTS FROM THE REST OF A MIXTURE

CROSS-REFERENCE TO RELATED APPLICATIONS

This application is a U.S. National Stage Application pursuant to 35 U.S.C. § 371 of International Patent Application PCT/EP2021/063199, filed on May 18, 2021, and published as WO 2021/233945 on Nov. 25, 2021, which claims priority to French Patent Application FR2005102, filed on May 19, 2020, all of which are incorporated herein by reference in their entireties for all purposes.

The present invention relates to the field of sorting insects, for example in particular in the context of rearing insects.

The insects concerned by the invention are crawling insects, or insects that are primarily crawling insects, for example Coleoptera, Isoptera, Blattoptera, Hemiptera and Heteroptera.

It finds a preferential application in the sorting of yellow mealworms, also called Tenebrio molitor.

Unless otherwise specified, the term "insect" is used to designate any developmental stage from the egg or ootheca to the adult insect. As detailed below, the invention relates to the sorting of a mixture containing adult insects or larvae having legs so as to separate them from the rest of that mixture.

The production of insects on a large scale has numerous advantages, in particular in the agro-industry. Some edible insect species are indeed rich in protein and may in particular serve for feeding animals, for fish, crustaceans, and some fowl. Large scale insect rearing also has advantages in other industrial sectors. For example, the exoskeleton of insects is in large part constituted by chitin, of which a known derivative is chitosan. The applications for chitin and/or chitosan are numerous: cosmetic (cosmetic composition), medical and pharmaceutical (pharmaceutical composition, treatment of burns, biomaterials, corneal plasters, surgical thread), dietary and food, technical (filtering agent, texturizer, flocculent or adsorbent for example in particular for filtering and decontaminating water), etc.

Document FR3034622 presents a farm configured to large-scale insect rearing, that is to say at industrial scale. The rearing therein employs rearing containers (typically tubs) which are stacked to form basic rearing units. The basic rearing units are stored in a first zone, and, when a rearing operation is to be carried out, the containers are brought to a station configured for performing the operation, grouped into basic rearing units or ungrouped on a unitary basis.

The rearing operations concern non-exhaustively feeding, provision of water, the grading of the insects, the addition of insects to rearing containers, and numerous and various sorting operations which, during rearing, enable the insects to be separated or classified according to their stage of development, or to separate live insects from dead insects and/or from their rearing medium, etc.

In this context, it proves in particular to be complex to sort live insects from dead insects, or adult insects from insects at immature stages. The sorting methods generally envisioned are manual methods which do not enable efficient and fast sorting on a large scale.

Imperfect solutions to this issue are proposed in document WO2019084554. This document discloses equipment for sorting insects, based on the principle whereby crawling insects have a capacity to cling onto a surface on which they move, with their legs. The items of equipment proposed in that document are nevertheless complex to implement industrially and/or prove imperfect in their sorting effectiveness.

Documents KR101464734 and EP3415002 also disclose sorting equipment based on this principle, which also prove to be of low effectiveness.

The invention developed is directed to providing an insect sorting device, in particular for separating adult insects or larvae, from other stages of growth and/or from inert components (dead insects, dejections, rearing medium), that is industrially applicable and effective.

Thus, the invention relates to an insect sorting device, comprising a belt conveyor having an upper surface and a lower surface formed by the belt of the conveyor. The device comprises a driving device configured to drive the belt of the conveyor, such that on operation of the conveyor the belt runs on the upper surface of a first end towards a second end of the conveyor where the belt is turned over to pass on the lower surface of the conveyor on which it runs from the second end towards the first end where the belt is turned over to pass again on the upper surface. The device also comprises a device enabling the deposit of a mixture comprising insects on the upper surface of the belt conveyor, such that on turning over of the belt at the location of the second end, all or some of the insects remain attached to the belt while the rest of the mixture falls by gravity. The device comprises a device for separating the insects making it possible to detach the insects attached to the lower surface of the conveyor. In the insect sorting device, as the upper surface of the conveyor being substantially flat and horizontal over a majority of its length between the first end and the second end, said upper surface of the conveyor comprises an end portion, adjacent the second end, having a downward inclination, comprised between 20° and 90° relative to the rest of the upper surface of the conveyor.

The invention thus provides an effective sorting system for separating the insects having legs from the rest of a mixture. This device is based on the capability of the insects having legs to attach themselves to the surface on which they move. This surface may be formed by an outside surface of a belt conveyor having suitable properties. When the belt of the conveyor turns over, that is to say at the time of its passage from the upper surface of the conveyor to the lower surface of the conveyor, the insects remain clinging onto the surface of the belt, that is to say on its outside surface, while the rest of the mixture which is sorted falls by gravity. This principle of sorting by belt conveyor that the insects cling onto, which is known in the state of the art, is greatly improved by the presence of an end portion having an inclination. This inclination has several beneficial effects on the quality of the sorting, that is to say on the proportion of the adult insects that remain clinging onto the belt of the conveyor when it turns over. Mainly, by inducing a beginning of falling or sliding of the insects on the belt, it incites them to cling onto it, such that when the belt turns over, the insects do not have to cling onto it very quickly. In general terms, this slope or inclination limits the sudden character of the turning over of the belt, which for example gives more time to the insects to cling on. Even when a slope 90° or close to 90° is employed, this limits the acceleration to which the insects are subjected on account of the change in direction of the belt, and enables better attachment of the insects. Furthermore, the slope enables certain insects that had been transported on the conveyor on their back, without having the possibility of clinging onto the belt, to turn over onto their legs.

In doing this, the sorting is improved and/or the running speed of the belt may be increased.

The inclination may more particularly be comprised between 30° and 70°, preferably between 45° and 60°. The end portion of the conveyor having an inclination may for example have a length comprised between twenty centimeters and one meter, measured along its upper surface. The device may comprise a means for adjusting the inclination.

The slope may thus be adapted to the sorting carried out, and be optimized according to multiple parameters: the species of insects sorted, their stage of development, the content of the mixture to sort, the type of belt used on the conveyor, the running speed of the belt, etc.

The belt may comprise an outside face having a structure configured for the attachment of the insects' legs.

The belt may comprise two distinct layers, one layer forming the outside face for the attachment of the insects' legs and an inside layer for reinforcing the belt.

The outside layer of the belt may be formed from a woven material. This woven material may have regular substantially square mesh elements having an opening of which the sides measure 110 microns to 1000 microns.

The belt employed on the belt conveyor is important for the sorting quality. As a matter of fact, the outside face of the belt (that is to say the visible face of the belt, whether it be above or below the conveyor) serves as an attachment surface for the insects. It must enable this attachment, through roughness and/or a suitably configured surface texture. The use of a fabric, for example a fabric of polyester or of polyamide (PA), gives good results. The thickness of the yarns and their number, defining the mesh size, is important. More particularly the mesh elements should be configured to the size of the hooks present at the ends of the legs of the insects to be sorted. The hook of an adult yellow mealworm leg for example measures of the order of 0.3 mm. The larvae have smaller hooks.

The separating device may be a blade or a brush extending transversely in relation to the belt, in immediate proximity to its surface.

A mechanical means for separating the insects that are clinging onto the belt enables an effective separation, without injuring the insects or damaging the belt of the conveyor.

The device may comprise a system for cleaning the belt generating a blade of compressed air that comes to impinge upon the belt of the conveyor at the location of its lower surface, between the separating device and the first end of the conveyor.

The cleaning of the belt is important for maintaining the surface state of the belt, which is fundamental for the sorting quality. As a matter of fact, as the outside face of the belt serves as an attachment surface for the insects, it is important for its roughness, or the texture of its surface, not to be altered over time. This is through a regular cleaning operation, i.e. a de-clogging operation, of the belt. However, it is also necessary for that cleaning not to alter the properties of the belt by mechanical wear, in particular by abrasion. The selection from among the technologies of cleaning by compressed air enables this issue to be addressed.

The device may furthermore comprise an extractor hood configured to suck away the air present above the upper surface of the conveyor. The presence of an extractor hood enables the collection of the lightest dust and particles present in the mixture to sort. To a certain degree, it enables the insects to be cleaned of fine particles that are liable to carry.

The device may comprise a casing enveloping the conveyor so as to limit the propagation of dust from the conveyor to outside the casing. This is particularly advantageous when an operation of cleaning the belt with compressed air is used.

The invention also relates to a machine for sorting insects comprising a first sorting device as described above and a second device as described above, in which said rest of the mixture falling by gravity from the conveyor of the first sorting device falls directly onto, or is brought onto, the upper surface of the conveyor of the second device.

The succession of several belt conveyors to carry out the sorting makes it possible to increase the proportion of insects recovered from the sorted mixture. With the device provided in the invention, properly optimized, the applicant has obtained a rate of recovery of the insects from the mixture of the order of 85% by mass with a conveyor having a single belt, and of the order of 95% by mass with two successive conveyors. This rate is satisfactory for rearing on a large scale. Of course, more than two successive conveyors may be employed to further improve the rate of recovery of the insects.

The invention also relates to the use of a device as described above or of a machine such as described above for the recovery of adult insects from a mixture comprising adult insects and insect larvae.

The invention also relates to a device as described above or a machine as described above for the recovery of the live insects from a mixture comprising live insects and dead insects.

The sorted insects may for example be yellow mealworm.

Still other features and advantages of the invention will appear in the following description.

In the accompanying drawings, given by way of non limiting example:

Figure 1:
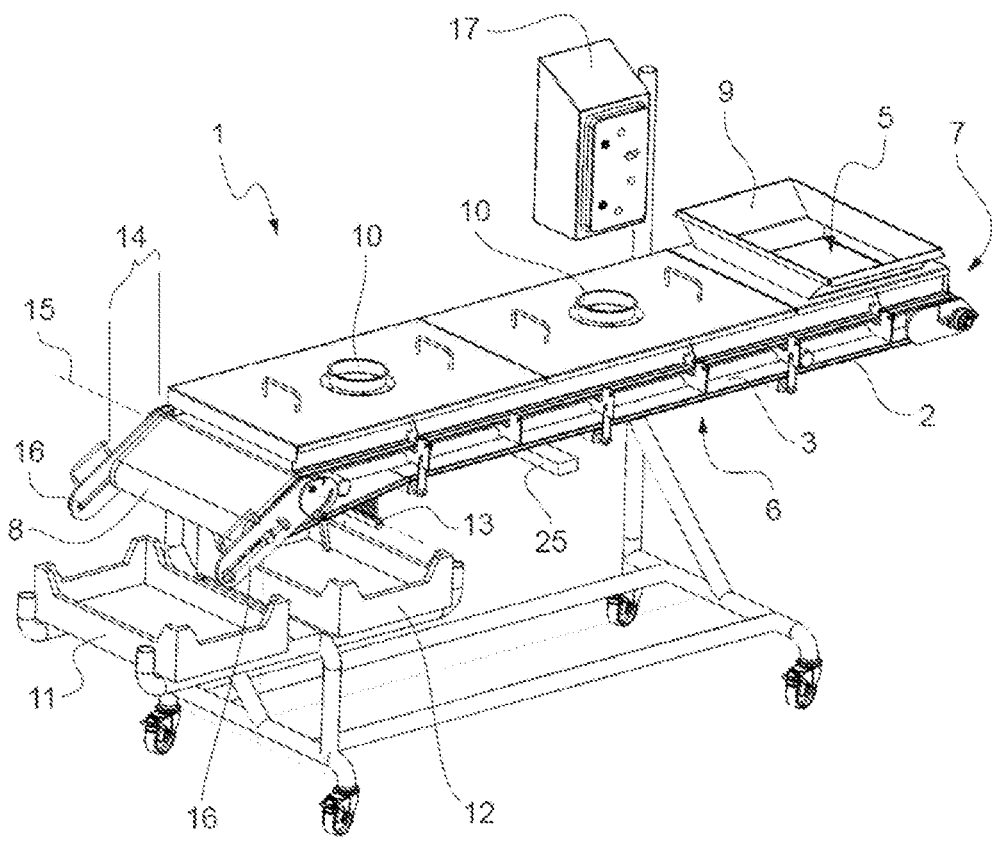
FIG. 1 shows, in a diagrammatic view in three dimensions, a sorting device in accordance with a first example embodiment of the invention.

FIG. 1 shows a sorting device 1 in accordance with a first example embodiment of the invention. The sorting device comprises a belt conveyor 2, which comprises a belt 3 driven by a driving device 4 enabling the belt 3 to be put into motion. The driving device 4 typically comprises a motor which rotates a shaft or roller for driving the belt 3.

The belt 3 forms a closed loop. For the conveyor 2 it constitutes an upper surface 5 and a lower surface 6. The upper surface 5 is the surface located on top of the conveyor enabling the transport of a product on the conveyor 2, between a first end 7 of the conveyor and a second end 8 of the conveyor. The lower surface 6 constitutes the return zone of the belt 3 between the second end 8 of the conveyor 2 and its first end. Each end of the conveyor constitutes a turning over zone of the 3. At the location of the first end 7 the belt 3 passes from the lower surface 6 to the upper surface 5 of the conveyor. At the location of the second end 8 the belt 3 passes from the upper surface 5 of the conveyor to the lower surface 6.

The device shown in FIG. 1 comprises a means facilitating the deposit of a product, in particular a mixture containing adult insects or larvae having legs, on the upper surface 5 of the conveyor 2. Here, an open hopper, or more generally a depositing tub 9 facilitating the deposit of a product on the belt 3 of the conveyor 2 is disposed in the vicinity of the first end 7 of the conveyor 2. An automatic or manual supply device may also be provided.

The product deposited on the upper surface 5 of the belt conveyor, i.e. a mixture comprising crawling insects (adults or larvae having legs), will thus be transported on the upper surface of the conveyor 2, on account of the running of the belt 3, to the second end 8. When this transport occurs, and according to the length of the conveyor, the mixture spreads on the surface of the conveyor and the insects present in the mixture tend to get onto their legs, if they were not already further to the deposit of the mixture on the belt 3. These phenomena may be promoted by optional vibrator means.

The transport time on the conveyor 2 may also be employed to de-dust the air and eliminate some of the finest particles present in the mixture, using extractor hoods. The extractor hoods are not shown in entirety in FIG. 1, but the embodiment of FIG. 1 has two hood apertures 10 at which the suction is carried out.

This suction also enables a degree of de-dusting of the insects present in the mixture.

When the mixture deposited on the belt 3 reaches the second end 8 of the conveyor 2, the insects attached to the belt 3 pass onto the lower surface 6 of the conveyor 2, while the rest of the mixture falls by gravity. The rest of the mixture falling by gravity may be received in a first recovery tub 11.

The insects attached to the belt 3 are recovered in a second recovery tub 12. For this, a device 13 for separating the insects is provided in superposed alignment with the second recovery tub 12. The separating device 13 may take various forms. It is a means for detaching the insects from the belt 3 in order for them to fall, without however injuring the insects and without the insects attaching to the separating means. The best results have been obtained with a blade, that is to say a thin rigid member, disposed substantially transversely relative to the belt 3 and to its running direction, and extending in immediate proximity to the belt 3, preferably however without touching it. Other separating devices may also be employed, such as a brush, or a jet of compressed air. The absence of contact with the belt 3 avoids the mechanical wear thereof. The clearance between the belt and the separating device should however not allow the passage or trapping of the insects. This clearance must therefore be small, for example of the order of the millimeter. Separation of the insects from the belt 3 by compressed air may also be envisioned.

When the device is in operative condition, the upper surface 5 of the conveyor is substantially horizontal, over a majority of its length, that is to say over a majority of the distance separating the first end 7 of the conveyor from its second end. The substantially horizontal orientation of the majority of the upper surface 5 of the conveyor may be obtained by arranging the support for the device on substantially horizontal ground. According to the invention, an end portion of the conveyor is however inclined. In particular, the end portion of the conveyor located at the second end 8 of the conveyor 2 has a downward inclination, that is to say that the second end 8 of the conveyor is located lower than the majority of the upper surface 5, or that the mixture arriving on that portion of the conveyor will descend before reaching the second end 8.

The inclination α of the end portion 14 (illustrated in FIG. 2) significantly improves the quality of the sorting.

This inclination incites the insects, through a reflex, to cling onto the belt to avoid them falling. It makes it possible to create a less abrupt turning over of the belt than in the absence of that slope, which leaves more time for the insects to attach onto the belt, and this reduces the acceleration to which the insects are subjected at the time the band turns over, at least at the start of this turning over. The inclination lastly makes it possible to assist some insects that had been transported on the conveyor on their backs, without having the possibility clinging onto the belt, to turn over onto their legs, on account of the discontinuity in the movement of the mixture to sort created by the slope.

In the example shown in FIG. 1, the inclination α is adjustable. For this, a tilting axis 15 enables the tilting, through a certain range of angles, of the end portion 14. In order to enable the adjustment of the slope without increasing or reducing the mechanical tension in the belt 3, but also for adjusting that tension, the end roller of the conveyor 2 located at the second end 8 is movable translationally between two adjusting arms 16 which tilt around the tilting axis 15. This device also enables the relaxing of the tension in the belt 3 in order to enable fast replacement thereof.

The inclination α, whether adjustable or not, may be comprised between 20° and 90°, for example between 30° et 70°, the best sorting results having been obtained for an inclination comprised between 45° and 60° relative to the horizontal, that is to say for example represented relative to the majority of the upper surface 5 of the conveyor 2. Whatever the case, at the time of use of the device, the upper surface 5 of the conveyor may conventionally define the horizontal.

The length of the end portion 14, measured along the upper surface of the conveyor, may for example be comprised between 20 cm and 1 m, for example of the order of 30 cm, which enables the aforementioned advantages to be obtained.

Lastly, the device of FIG. 1 is provided on a rigid support structure. The support structure of the example shown is a simple, mobile, structure, the device itself being relatively simple and light. Any other type of suitable support structure may be employed.

In the example shown, the support structure also makes it possible to bear the control and adjustment means 17 of the device.

In such a device, the operating parameters are important, to ensure a sufficient sorting speed for rearing at very large scale, combined with a desired effectiveness of the sorting.

The running speed is thus configured to the function of sorting insects. The running speed is configured to give sufficient time to the insects deposited on the belt conveyor to attach onto an outside surface of the belt of the conveyor.

In particular, a running speed of the belt of the order of 10 meters per minute to 30 meters per minute, for example of the order of 15 meters per minute or 20 meters per minute, gives good results.

The constitution of the belt is also important. More particularly the belt must have a surface state on its outside surface that is configured for the attachment of the insects. An appropriate surface state may be obtained with various industrial fabrics, for example a polyester (PES) or polyamide fabric. Nevertheless, the belt 3 must also be wear-resistant in order not to have to perform replacements too often. This is why an assemblage of two layers to constitute the belt may be advantageous, that is to say one layer to form the outside face which is configured for the attachment of the insects, and one layer to form the inside face of the belt 3 which is resistant to wear, in particular to abrasion.

For example, the belt 3 may comprise a belt of PES 120/34 fabric (that is to say having mesh element openings of 120 microns and an open surface area of 34% of the total surface area) for the outside face of the belt 3 and a belt of PES 1000/35 fabric (mesh elements of 1 mm and an open surface area of 35%) for the inside face of the belt 3.

The material, for example the fabric, constituting the outside face of the belt 3 may be configured according to the sorting operation performed with the device, according to the species of insects sorted and/or the stage of growth of the sorted insects. The material and in particular its surface state must be configured for the attachment of the insects by the hooks of their legs. For the adult yellow mealworm, which is the species preferentially sorted using the invention, these hooks measure approximately 0.3 mm. The larvae of yellow mealworm have hooks that are appreciably smaller.

Other fabrics have been tested with success. For sorting adult yellow mealworm, fabrics formed from yarns of 250 microns to 500 microns in diameter have been tested with success. Fabrics having mesh elements with an opening of 650 microns to 1 mm, with an open surface area of the order of 50% to 65% of their total surface area have proved particularly suitable. Other fabrics can of course be envisioned.

For sorting a mixture containing larvae of yellow mealworm, fabrics formed from finer yarns, of the order of 35 microns to 80 microns, have proved suitable. Fabrics having mesh elements with an opening of 85 microns to 150 microns, in particular from 110 to 150 microns, with an opening surface area of the order of 30% to 50% of their total surface area have proved particularly suitable. Other fabrics may of course be envisioned.

More generally, for sorting larvae or adult insects, fabrics having the following properties have proved appropriate. an opening of the mesh elements of 110 to 1000 µm, a diameter of the constituent yarns of 80 to 500 µm, an opening surface area of 31% to 64% of the total surface area.

Metal strips, following an analogous mesh structure, have also been tested successfully. Lastly, the surface state configured for the attachment of the insects may result from the presence of asperities, teeth, bristles, or other forms of roughness, at the surface of the belt 3.

By optimizing the device described above, a rate of separation of approximately 85% by mass of the insects is obtained (i.e. the effectiveness obtained for the separation of the live insects relative to the dead insects, in an initial mixture comprising of the order of 95% by mass of live insects and dead insects, and less than 5% of dejections and of rearing substrate and other similar components). This means that 85% of the mass of insects to be separated from the mixture (adults, nymphs having legs) initially present in the mixture and which is deposited on the conveyor are properly separated from that mixture by the device.

By manipulating certain parameters, for example the running speed of the belt, a slightly higher separation rate may be obtained, but that rate (of the order of 90%) is not entirely satisfactory in the context of rearing providing good performance at large scale.

This is why, according to a second aspect that has been developed in the invention, there is provided a sorting machine comprising several devices operating according to the principle described with reference to FIG. 1.

Figure 2:
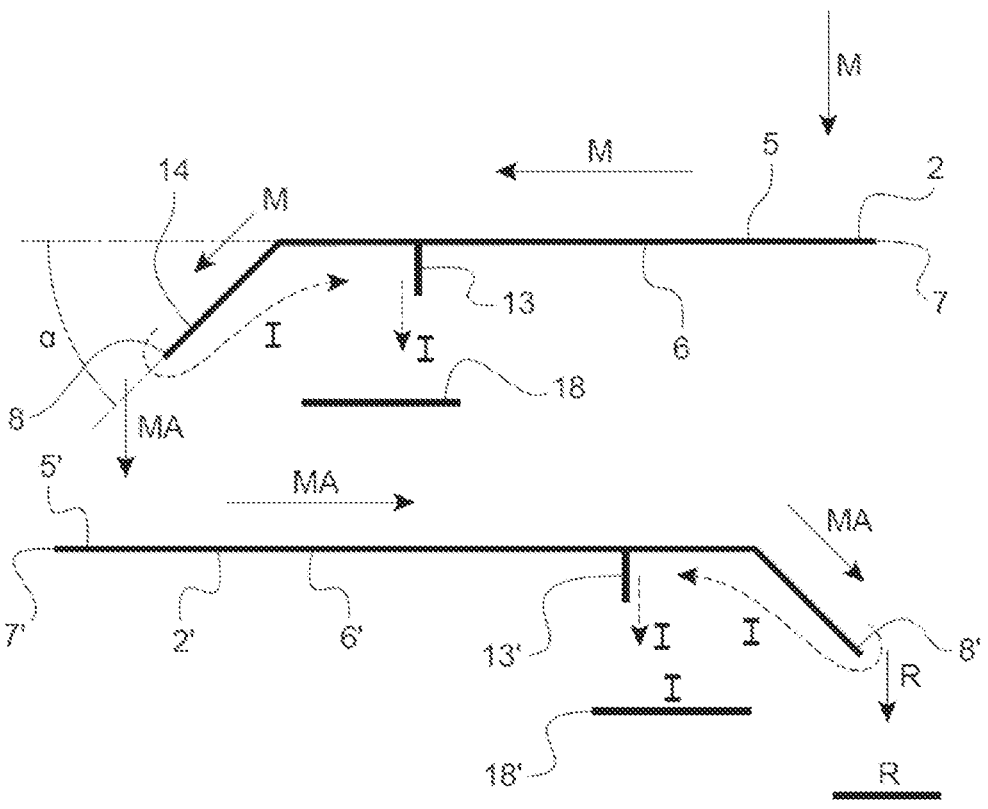
FIG. 2 shows, based on a diagram of principle, the flows in a sorting machine in accordance with an example embodiment of the invention.

FIG. 2 is a figure of principle directed to illustrating the flows in such a machine.

A mixture M comprising crawling insects is deposited on a belt conveyor 2, on its upper surface 5, in the vicinity of its first end 7.

In addition to insects that it is desired to separate from the rest of the mixture, the mixture M may comprise, non-exhaustively, insects that are at other stages of their development than the sorted insects (eggs, larvae, nymphs, when the sorting is directed to separating adults, eggs and nymphs when the sorting is directed to separating the larvae), dead insects, insect dejections, and rearing substrate (that is to say the product in which the insects are reared, which may contain the food necessary for their growth).

The mixture M is transported towards the second end 8 of the conveyor. Before reaching that second end 8, the mixture reaches the inclined end portion 14 of the conveyor 2, which assists the insects in clinging onto the belt of the conveyor 2.

At the location of the second end 8 where the belt of the conveyor turns over to pass onto the lower surface 6, a large portion of the insects I remains attached to the belt of the conveyor, while the rest of the mixture, i.e. an insect-depleted mixture MA, falls by gravity.

The insects I are detached from the belt by a separating device 13 and fall onto a reception surface 18 (which may for example be the second recovery tub 12 of FIG. 1). As indicated earlier, 85% approximately of the insects initially present in the mixture M may thus be recovered.

The depleted mixture MA falls onto the upper surface 5' of a second conveyor 2', on its belt 3', in the vicinity of its first end 7'.

The depleted mixture MA is transported to the second end 8' of the second conveyor 2'. Before reaching this second end 8', the mixture reaches the inclined end portion 14' of the second conveyor 2', which assists the insects in clinging onto the belt of the second conveyor 2'.

At the location of the second end 8' where the belt of the second conveyor 2' turns over to pass onto the lower surface 6', a substantial portion of the insects I present in the depleted mixture remain hooked onto the belt of the second conveyor 2', while the rest of the mixture, i.e. the rest R of the depleted mixture MA, falls by gravity.

The insects I are detached from the belt by a second separating device 13' and fall onto a second reception surface 18' (for example a second recovery tub).

In doing this, the overall proportion of insects separated from the initial mixture M reaches 95% by mass or even more.

Figure 3:
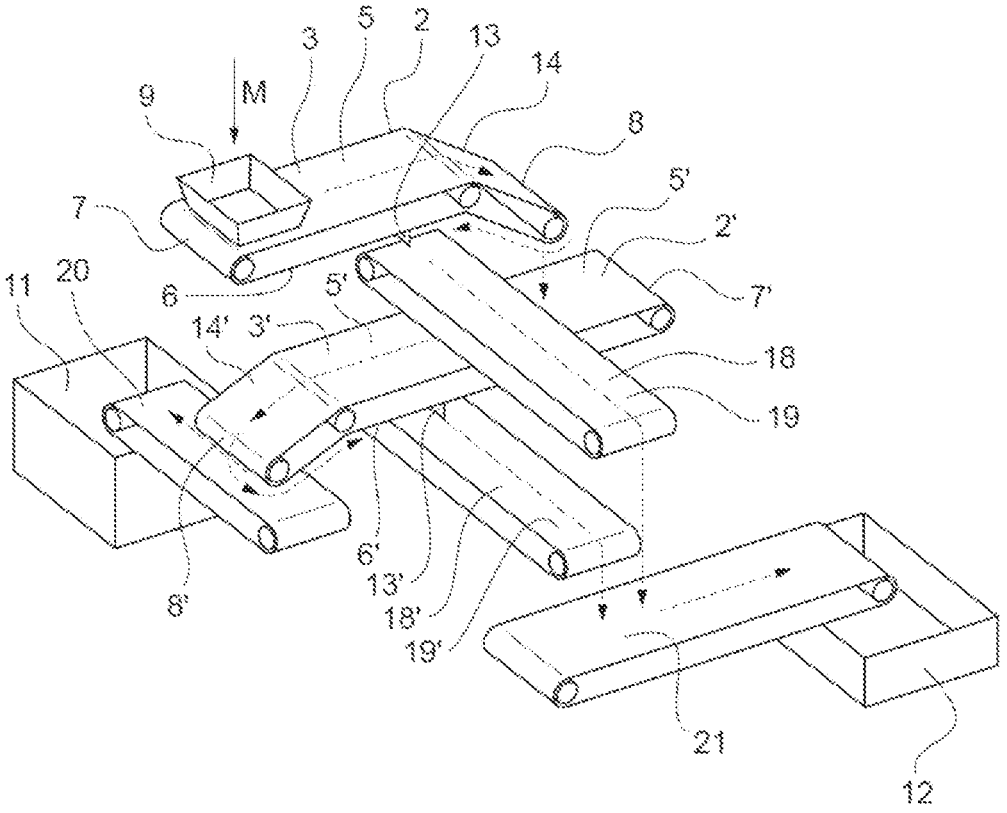
FIG. 3 shows, in a diagrammatic view in three dimensions, the main members of a machine in accordance with an embodiment of the invention.

FIG. 3 shows a diagrammatic view in three dimensions of the main parts of a sorting machine implementing the streams presented in FIG. 2.

The machine of FIG. 3 thus comprises a conveyor 2, provided with a depositing tub 9 making it possible to deposit the mixture to sort on the upper surface of the conveyor 2, on the belt 3. The sorting, i.e. the separation of the insects present in the mixture, is carried out as described with reference to FIGS. 1 and 2. Remarkably, the reception surface 18 for the insects separated by the sorting device is itself formed by a first belt conveyor 19 for receiving insects.

The rest of the mixture, which is a mixture depleted in insects, falls onto a second conveyor 2'. The sorting of the depleted mixture, i.e. the separation of the insects present in the depleted mixture, is carried out as described with reference to FIG. 2. Remarkably, the second reception surface 18' for the insects separated by this second sorting device is itself formed by a second belt conveyor 19' for receiving insects.

The rest of the depleted mixture, which is practically or totally depleted of live insects, falls onto a belt conveyor for collecting the remainder 20, which transports that remainder to, in the example shown, a first recovery tub 11.

The first belt conveyor 19 for receiving insects and the second belt conveyor 19' for receiving insects transport the insects in order to collect them on a belt conveyor for collecting insects 21. At the end of this belt conveyor for collecting insects 21, the insects fall, in the example shown, into a second recovery tub 12.

Figure 4:
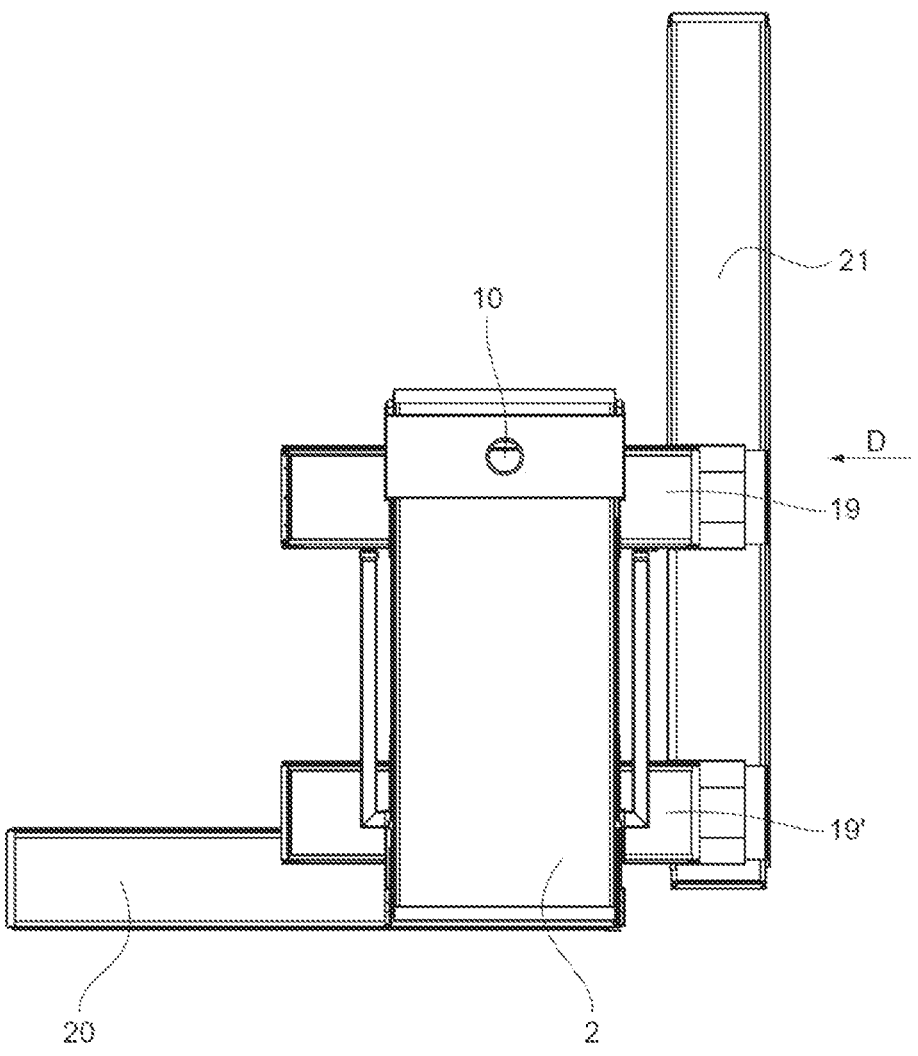
FIG. 4 shows, in a simplified plan view, a machine corresponding to the machine of FIG. 3.
Figure 5:
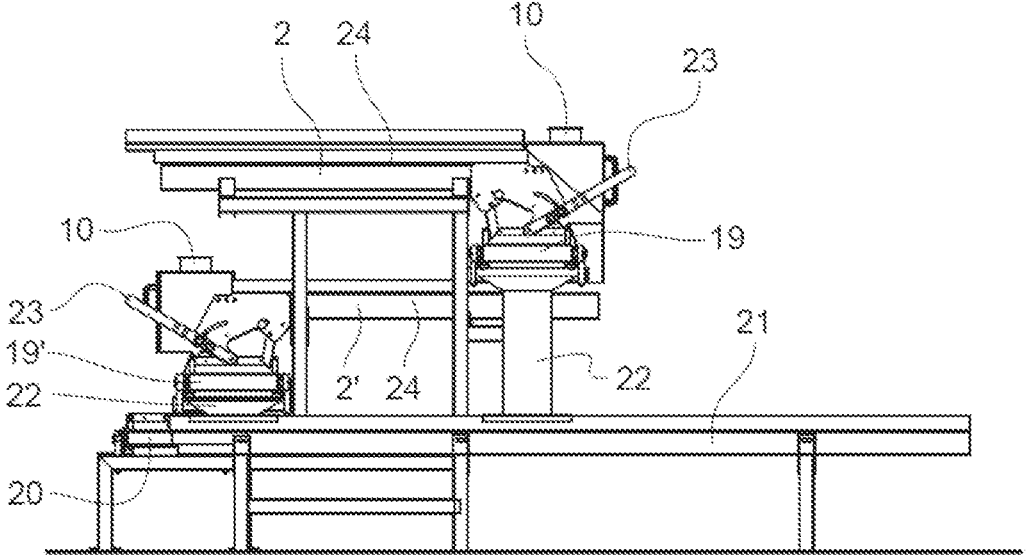
FIG. 5 shows, in a simplified side view, the machine of FIGS. 3 and 4.

FIG. 4 shows, in a simplified plan view, a machine corresponding to the machine of FIG. 3. FIG. 5 shows the machine of FIG. 4, in a side view, in the direction D mentioned in FIG. 4.

FIGS. 4 and 5 make it possible to view a concrete example of configuration of a machine comprising two successive sorting devices.

Thus, the conveyor 2 and the second conveyor 2' are superposed, at a distance from each other, and have a slight longitudinal offset relative to each other in order for the rest of the mixture (that is to say the insect-depleted mixture) falling by gravity from the conveyor 2 to fall onto the second conveyor 2'. The conveyor 2 and the second conveyor 2' are configured such that the belt of the conveyor 2 and the belt of the belt of the second conveyor 2' are driven in opposite directions. This affords better compactness to the machine.

The belt conveyor 2 and the second belt conveyor 2' may, for example, have a width of the order of 30 cm to 1.5 m, for example of the order of 1 m. The belt conveyor 2 and the second belt conveyor 2' may, for example, have a total length comprised between 1 m and 10 m, for example of the order of 3 m. These dimensions are also suitable for the embodiment shown in FIG. 1.

The first belt conveyor 19 for receiving insects and the second belt conveyor 19' for receiving insects extend substantially at a right angle to said conveyor 2 and the second conveyor 2', in planes of different heights, configured for the height of the conveyor from which they recover the insects. At the end of the first belt conveyor 19 for receiving insects and of the second belt conveyor 19' for receiving insects there is provided a descent chute 22 for the insects enabling the insects to be guided in their descent onto the belt 21 for collecting the insects.

In the sorting machine example shown here, each of the first conveyor 2 and the second conveyor 2' comprises an adjusting lever 23 enabling the inclination of the end part of the belt conveyor to be modified.

The machine shown is equipped with extractor hoods, connected to the hood apertures 10. To contain dust in the machine, it may be equipped, as in the example shown, with casings 24 around each belt conveyor (or some of them). The casings 24 are advantageously provided with quick dismantling or opening means, in order to facilitate the replacement of the belt of the conveyor and to shorten the time of that operation.

Alternatively or additionally, a general casing may be formed around the whole of the sorting machine.

Such casings are important when the belt conveyor or conveyors are equipped with a compressed air blade cleaning device. Such a cleaning device enables the cleaning of the belt of a conveyor by projecting onto it a stream of high pressure air, over a very small surface transverse to the belt. The use of this cleaning device proves particularly advantageous in a device or machine in accordance with the invention, since it enables cleaning of the belt, and particularly for example unclogging of the outside face of the belt enabling the attachment of the insects, without damaging the belt and even without altering the surface state of the belt, which is fundamental for ensuring the attachment properties and thus the desired sorting.

A device 25 for cleaning with a compressed air blade is shown diagrammatically in FIG. 1, to illustrate a preferred position thereof in the device. The compressed air blade cleaning device 25 is thus positioned on the lower face of the conveyor, downstream of the separating device 13.

The invention thus developed enables various sorting operations to be carried out in a large-scale farm for rearing crawling insects. It enables effective separation of the crawling insects (adult or larvae having legs) present in a mixture, from the rest of the mixture.

Compared with the machines of the prior art based on the same sorting principle whereby the insects tend to attach themselves to a moving surface on which they are in movement, the present invention significantly improves the sorting effectiveness.

The invention is thus particularly well adapted to the recovery of adult insects from a mixture comprising adult insects and insect larvae, as well as the recovery of the live adult insects from a mixture comprising live adult insects and dead insects (whether from the same sorting process or from distinct sorting processes.) Although applicable to numerous species, it finds a preferential application to rearing yellow mealworm.

The invention claimed is:

1. A device for sorting crawling insects having legs, comprising a support structure and:

a belt conveyor (2) having an upper surface (5) and a lower surface (6) formed by a belt (3) of the conveyor (2), the belt (3) of the conveyor (2) comprising an outside face having a surface state configured for attachment of the insects' legs a driving device configured to drive the belt (3) of the conveyor (2), such that on operation of the conveyor (2) the belt (3) runs on the upper surface of a first end (7) towards a second end (8) of the conveyor where the belt (3) is turned over to pass on the lower surface (6) of the conveyor (2) on which the belt runs from the second end (8) towards the first end (7) where the belt (3) is turned over to pass again on the upper surface (5), the device comprising a deposit tub for the deposit of a mixture comprising insects on the upper surface (5) of the belt conveyor (2), such that on turning over of the belt (3) at the second end (8), all or some of the insects remain attached to the belt (3) while a rest of the mixture falls by gravity, a blade or a brush extending transversely in relation to the belt (3), in immediate proximity to the surface of the belt (3) to detach the insects attached to the lower surface (6) of the conveyor (2), wherein as the upper surface (5) of the conveyor (2) being flat and horizontal over a majority of a length between the first end (7) and the second end (8), said upper surface (5) of the conveyor (2) comprises an end portion (14), adjacent the second end (8), having a downward inclination ($\alpha$), comprised between 20° and 90° relative to a rest of the upper surface (5) of the conveyor (2).

2. The device according to claim 1, wherein the downward inclination ($\alpha$) is comprised between 30° and 70°.

3. The device according to claim 1, wherein the end portion (14) of the conveyor (2) having the downward inclination ($\alpha$) has a length comprised between twenty centimeters and one meter, measured along the upper surface of the conveyor (2).

4. The device according to claim 1, comprising a mechanism for adjusting the downward inclination ($\alpha$).

5. The device according to claim 1, wherein the outside face of the belt (3) is formed from a woven material.

6. The device according to claim 5, wherein the woven material has regular square mesh elements having an opening of which sides measure 110 microns to 1000 microns.

7. The device according to claim 1, wherein the driving device is configured to drive the belt (3) of the conveyor (2) at a running speed comprised between 10 m/s and 30 m/s.

8. The device according to claim 1, comprising a system for cleaning the belt (3) generating a blade of compressed air that comes to impinge upon the belt (3) of the conveyor (2) on the lower surface (6) of the conveyor, between the separating device and the first end (7) of the conveyor (2).

9. The device according to claim 1, further comprising an extractor hood configured to suck away air present above the upper surface (5) of the conveyor (2).

10. The device according to claim 1 comprising a casing enveloping the conveyor (2) so as to limit a propagation of dust from the conveyor (2) to outside the casing.

11. The machine for sorting insects comprising a first sorting device according to claim 1 and a second device according to claim 1, in which said rest of the mixture falling by gravity from the conveyor (2) of the first sorting device falls directly onto, or is brought onto, the upper surface (5) of the conveyor (2) of the second device.

12. A method of recovering adult insects from a mixture comprising adult insects and insect larvae comprising using a device according to claim 1 or of a machine for sorting insects comprising a first sorting device according to claim 1 and a second device according to claim 1, in which said rest of the mixture falling by gravity from the conveyor (2) of the first sorting device falls directly onto, or is brought onto, the upper surface (5) of the conveyor (2) of the second device.

13. The method according to claim 12, wherein the insects are yellow mealworm.

14. A method of recovering live insects from a mixture comprising living insects and dead insects comprising using a device according to claim 1 or of a machine for sorting insects comprising a first sorting device according to claim 1 and a second device according to claim 1, in which said rest of the mixture falling by gravity from the conveyor (2) of the first sorting device falls directly onto, or is brought onto, the upper surface (5) of the conveyor (2) of the second device.

15. The method according to claim 14, wherein the insects are yellow mealworm.

16. The device according to claim 1, wherein the downward inclination ($\alpha$) is comprised between 45° and 60°.

* * * * *